US009012683B2

(12) United States Patent
Wellman, Jr. et al.

(10) Patent No.: US 9,012,683 B2
(45) Date of Patent: Apr. 21, 2015

(54) COPRODUCTION OF ACETIC ACID AND ACETIC ANHYDRIDE

(75) Inventors: Gregory Abbott Wellman, Jr., Kingsport, TN (US); Brandon Tyler Earls, Kingsport, TN (US); Robert Sterling Kline, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 90 days.

(21) Appl. No.: 13/289,518

(22) Filed: Nov. 4, 2011

(65) Prior Publication Data
US 2012/0123156 A1 May 17, 2012

Related U.S. Application Data

(60) Provisional application No. 61/413,214, filed on Nov. 12, 2010.

(51) Int. Cl.
C07C 51/10 (2006.01)
C07C 51/12 (2006.01)
C07C 51/54 (2006.01)

(52) U.S. Cl.
CPC ............ C07C 51/12 (2013.01); C07C 51/54 (2013.01)

(58) Field of Classification Search
CPC .................... C07C 51/12; C07C 51/54
USPC .......................................... 562/517
See application file for complete search history.

(56) References Cited

U.S. PATENT DOCUMENTS

| | | | |
|---|---|---|---|
| 3,772,360 A | 11/1973 | Paulik et al. | |
| 3,927,078 A * | 12/1975 | Lapporte et al. | 560/232 |
| 4,039,395 A | 8/1977 | Eby | |
| 4,046,807 A * | 9/1977 | Kuckertz | 562/891 |
| 4,115,444 A * | 9/1978 | Rizkalla | 562/891 |
| 4,252,741 A * | 2/1981 | Porcelli et al. | 562/891 |
| 4,333,884 A | 6/1982 | Kubbeler et al. | |
| 4,358,411 A | 11/1982 | Porcelli et al. | |
| 4,366,259 A | 12/1982 | Knifton et al. | |
| 4,374,070 A * | 2/1983 | Larkins et al. | 562/891 |
| 4,417,077 A | 11/1983 | Drago et al. | |
| 4,430,273 A * | 2/1984 | Erpenbach et al. | 562/891 |
| 4,559,183 A * | 12/1985 | Hewlett | 562/891 |
| 4,629,809 A | 12/1986 | Vanderpool et al. | |
| 5,003,104 A * | 3/1991 | Paulik et al. | 562/517 |
| 5,144,068 A | 9/1992 | Smith et al. | |
| 5,155,261 A | 10/1992 | Marston et al. | |
| 5,258,549 A | 11/1993 | Pimblett | |
| 5,292,948 A * | 3/1994 | Zoeller et al. | 562/891 |
| 5,298,586 A | 3/1994 | Beevor et al. | |
| 5,380,929 A | 1/1995 | Erpenbach et al. | |
| 5,416,237 A | 5/1995 | Aubigne et al. | |
| 5,442,107 A | 8/1995 | Beevor et al. | |
| 5,488,143 A | 1/1996 | Uhm et al. | |
| 5,510,524 A | 4/1996 | Garland et al. | |
| 5,648,531 A | 7/1997 | Morimoto et al. | |
| 5,880,311 A | 3/1999 | Uemura et al. | |
| 5,900,505 A | 5/1999 | Tustin et al. | |
| 5,922,911 A | 7/1999 | Jones et al. | |
| 6,080,373 A | 6/2000 | Uemura et al. | |
| 6,130,355 A | 10/2000 | Jones | |
| 6,211,405 B1 | 4/2001 | Cheung et al. | |
| 6,452,043 B1 | 9/2002 | Zoeller et al. | |
| 6,667,418 B2 | 12/2003 | Broussard et al. | |
| 6,916,951 B2 | 7/2005 | Tustin et al. | |
| 6,992,212 B2 | 1/2006 | Zehner et al. | |
| 7,115,774 B2 | 10/2006 | Magna et al. | |
| 7,737,298 B2 | 6/2010 | Kline et al. | |
| 2007/0287862 A1 | 12/2007 | Kline et al. | |

FOREIGN PATENT DOCUMENTS

| | | | | |
|---|---|---|---|---|
| EP | 0 153 834 | A1 | 9/1965 | |
| EP | 0 338 730 | A1 | 10/1969 | |
| EP | 0 008 396 | A1 | 3/1980 | |
| EP | 0 081 152 | A1 | 6/1983 | |
| EP | 0 087 869 | A1 | 9/1983 | |
| EP | 0 087 870 | A1 | 9/1983 | |
| EP | 0087870 | A1 * | 9/1983 | ............ C07C 51/56 |
| EP | 87870 | A1 * | 9/1983 | ............ C07C 51/12 |
| EP | 0087870 | A1 * | 9/1983 | |
| EP | 0 109 212 | A1 | 5/1984 | |
| EP | 0 096 974 | B1 | 9/1985 | |
| EP | 0 391 680 | A1 | 10/1990 | |
| EP | 0 584 964 | A1 | 3/1994 | |
| EP | 0 752 406 | A1 | 1/1997 | |
| EP | 0 976 711 | A1 | 2/2000 | |
| GB | 2 029 409 | A | 3/1960 | |
| GB | 1 234 641 | A | 6/1971 | |
| JP | 2003-146933 | A | 5/2003 | |

(Continued)

OTHER PUBLICATIONS

Notification of Transmittal of the International Search Report and the Written Opinion of the International Searching Authority, or the Declaration received in International Application No. PCT/US2011/059954 date of mailing Feb. 17, 2012.

(Continued)

*Primary Examiner* — Fereydoun G Sajjadi
*Assistant Examiner* — Kofi Adzamli
(74) *Attorney, Agent, or Firm* — William K. McGreevey

(57) ABSTRACT

Disclosed is a process for the coproduction of acetic acid and acetic anhydride by producing in a first carbonylation reactor a carbonylation product mixture containing acetic anhydride, removing the carbonylation mixture from the first carbonylation reactor, contacting the carbonylation mixture with methanol to react with and convert some or all of the acetic anhydride contained in the mixture to acetic acid and methyl acetate, feeding the resulting reaction composition to a second carbonylation reactor and contacting the reaction composition to carbonylation.

28 Claims, No Drawings

(56) References Cited

FOREIGN PATENT DOCUMENTS

| WO | | 99/54273 | A1 | | 10/1999 | |
| WO | WO | 99/54273 | | * | 10/1999 | |
| WO | WO | 9954273 | A1 | * | 10/1999 | .............. C07C 51/56 |

OTHER PUBLICATIONS

Bertleff, Werner; "Carbonylation"; Ulmann's Encyclopedia of Industrial Chemistry, 6$^{th}$ Edition, vol. 6; 2003; pp. 473-491; Wiley-VCH Verlag GmbH & Co. KGaA; Weinheim, Germany.

De Blasio, N. et al.; "Activity and Stability of Two Polymer-Supported Rhodium-Based Catalysts for the Vapour Phase Carbonylation of Methanol"; Journal of Catalysis, 176; Jan. 1998; pp. 253-259.

Howard, M.J. et al; "C$_1$ to acetyls: catalysis and process"; Catalysis Today, 18; 1993; pp. 325-354.

Riemenschneider, Wilhelm; "Carboxylic Acids, Aliphatic"; Ulmann's Encyclopedia of Industrial Chemistry, 6$^{th}$ Edition, vol. 6; 2003; pp. 493-507; Wiley-VCH Verlag GmbH & Co. KGaA, Weinheim, Germany.

Roth, James F. et al.; "Low Pressure Process for Acetic Acid via Carbonylation"; Chem Tech; Oct. 1971; pp. 600-605.

Sunley, Glenn J. and Watson, Derrick J.; "High productivity methanol carbonylation catalysis using iridium The Cativa™ process for the maufacture of acetic acid"; Catalysis Today, 58; 2000; pp. 293-307.

Yoneda, Noriyuki et al.; "Recent advances in processes and catalysts for the production of acetic acid"; Applied Catalysis A: General, 221; 2001; pp. 253-265.

Notification of Transmittal of the International Search Report and the Written Opinion of the International Searching Authority, or the Declaration date of mailing Dec. 19, 2007 received in International Application No. PCT/US2007/012457.

* cited by examiner

COPRODUCTION OF ACETIC ACID AND ACETIC ANHYDRIDE

CROSS-REFERENCE TO RELATED APPLICATION

This application claims priority to U.S. Provisional Patent Application No. 61/413,214 filed Nov. 12, 2010.

FIELD OF THE INVENTION

This invention pertains to a process for the coproduction of acetic acid and acetic anhydride. More specifically, this invention pertains to the production of acetic acid and acetic anhydride by producing in a first carbonylation reactor a first reaction product composition containing acetic anhydride, removing the first reaction product composition from the first carbonylation reactor, contacting the first reaction product composition with methanol in an esterification zone to react with and convert some or all of the acetic anhydride contained in the composition to acetic acid and methyl acetate, feeding the resulting reaction composition to a second carbonylation reactor and contacting the reaction composition with carbon monoxide to result in carbonylation.

BACKGROUND OF THE INVENTION

The production of acetic anhydride by contacting in the liquid phase a composition containing methyl acetate and/or dimethyl ether and one or more iodine-containing compounds with carbon monoxide in the presence of a carbonylation catalyst has been reported extensively in the patent literature. See, for example, U.S. Pat. Nos. 3,927,078; 4,046,807; 4,115,444; 4,252,741; 4,374,070; 4,430,273; 4,559,183; 5,003,104; and 5,292,948 and European Patents 8396; 87,869; and 87,870.

In many processes involving coproduction of acetic acid and acetic anhydride, methanol and methyl acetate are fed to a primary carbonylation reactor and products are produced in the presence of CO in one reactor. In such processes, all of the heat of reaction is released in the single reactor. The heat of reaction for methanol carbonylation is quite high, e.g., about twice that of the heat of reaction for methyl acetate carbonylation. Thus, a large amount of heat must be removed from the primary carbonylation reactor under severe conditions of high pressure and a corrosive environment. Furthermore, the reactions that form acetic acid and acetic anhydride occur simultaneously, leaving no opportunity to sequence the reactions in such a way as to allow the exothermic reactions to occur separately. Methods of sequencing the reaction are thus desirable.

BRIEF SUMMARY OF THE INVENTION

The invention provides processes for the coproduction of acetic anhydride and acetic acid in the liquid phase under substantially anhydrous conditions which includes the steps of:

(1) continuously combining in a first carbonylation reactor components including: (i) at least one feedstock compound selected from methyl acetate, dimethyl ether or a combination thereof; and (ii) a first carbon monoxide stream, to produce a first liquid reaction composition in a liquid phase, wherein:
the components are combined in the presence of a carbonylation catalyst,
the components are combined under conditions effective to convert at least some of the feedstock compound to acetic anhydride, and
the first liquid reaction composition contains: (i) at least some unreacted feedstock compound, (ii) dissolved carbon monoxide and (iii) acetic anhydride product;

(2) continuously removing at least part of the first liquid reaction composition from the first carbonylation reactor and contacting the at least part of the first liquid reaction composition with methanol in an esterification zone to form a second liquid reaction composition in a liquid phase under conditions effective to cause at least some of the acetic anhydride from the first reaction composition and at least some of the methanol to react to produce methyl acetate and acetic acid in the second liquid reaction composition;

(3) continuously feeding the second liquid reaction composition to a second carbonylation reactor along with additional carbon monoxide to produce a third liquid reaction composition in a liquid phase, wherein:
the second liquid reaction composition and a second carbon monoxide stream are combined under conditions effective to cause at least some unreacted feedstock compound, methyl acetate from (2), or both to be converted to acetic anhydride, and
the third reaction composition contains (i) unreacted feedstock compound, methyl acetate from (2) or both, (ii) acetic acid, and (iii) acetic anhydride product, and (4) continuously removing the third liquid reaction composition from the second carbonylation reactor.

In some embodiments, the esterification zone includes at least one heat exchanger configured to remove some heat from the liquid reaction composition, the second liquid reaction composition, or both. In some embodiments, the at least one heat exchanger converts water into steam.

In some embodiments, at least one of the carbonylation reactors is operated at a temperature of about 100 to about 300° C. and a pressure (total) of about 21.7 to about 276.7 bars absolute (bara) and the residence time within the carbonylation reactors is about 4 minutes to about 120 minutes. In some embodiments, the carbonylation reactors are operated at a temperature of about 175 to 220° C. and a pressure (total) of about 35.5 to about 104.4 bara, the residence time within the carbonylation reactors is about 15 to about 40 minutes, the composition of the first reaction composition removed from the first carbonylation reactor and fed to the esterification zone of step (2) is about 8 to about 38 weight percent acetic anhydride, about 15 to about 60 weight percent feedstock compound, about 6 to 25 weight percent methyl iodide, about 18 to about 40 weight percent acetic acid.

In some embodiments, the amount of methanol fed to the esterification zone is about 0.6 to about 0.85 moles per mole of acetic anhydride fed via the first reaction composition to the esterification zone. In some embodiments, the amount of methanol fed to the esterification zone is above zero but less than about 1 moles per mole of acetic anhydride fed via the first reaction composition to the esterification zone. In some embodiments, the amount of methanol fed to the esterification zone is sufficient to create a stoichiometric excess of moles of methanol against the moles of acetic anhydride fed to the esterification zone.

In some embodiments, the process further includes feeding acetic acid to the first carbonylation reactor. In some embodiments, the components combined in the first carbonylation reactor further include at least one iodine-containing compound. In some embodiments, wherein the at least one iodine-containing compound is methyl iodide or a compound that forms methyl iodine in the first liquid reaction composition.

In some embodiments, the carbonylation catalyst contains rhodium or a rhodium compound. The process of any of claims 1-12, wherein at least some of the carbonylation catalyst dissolves in the first liquid reaction composition. In some embodiments, at least some of the carbonylation catalyst is a solid in the presence of the first liquid reaction composition.

In some embodiments, the first carbon monoxide stream is fed at a location inside the first liquid reaction composition. In some embodiments, the second carbon monoxide stream is fed at a location inside the third liquid reaction composition.

DETAILED DESCRIPTION

The invention provides flexibility in the operation of carbonylation processes by allowing some of the acetic anhydride product resulting from a carbonylation process to be converted to acetic acid and methyl acetate in between two carbonylation reactors. The conversion occurs in an esterification zone by combining the product from a first carbonylation process with methanol prior to introduction of the product into the second carbonylation process. In some embodiments, the esterification zone includes one or more heat exchangers, allowing transfer of heat from the composition in the heat exchanger.

In some embodiments, the coolant fed to the heat exchanger is water that is converted to steam to recover the heat generated by the exothermic carbonylation and esterification reactions.

The process of the present invention provides a means for modifying a methyl acetate carbonylation process which produces primarily acetic anhydride to a process that produces a combination of acetic acid and acetic anhydride, e.g., acetic acid/acetic anhydride blends, in some embodiments blends in weight ratios of about 1:1.5 to about 20:1. Esterification reactions with methanol allows converting some of the acetic anhydride to acetic acid at a location outside the reactors where heat can be removed from the process, in some embodiments in ways that allow use of the heat to generate process steam. In addition, in some embodiments the esterification reaction produces additional feed material for carbonylation (methyl acetate), which improves the space time yield, i.e., the productivity, of the process by shifting the reaction mixture in a manner that can drive higher reaction rates in the second carbonylation reactor.

Carbonylation Steps

In each carbonylation step of the process, the following components are combined in a carbonylation reactor under conditions effective to cause carbonylation: (i) a feedstock compound, and (ii) carbon monoxide. In some embodiments, the carbon monoxide is fed inside the liquid phase of the liquid reaction medium (e.g., on the liquid side of any liquid/gas interface in the reactor or below the upper surface of the liquid). The conditions cause carbonylation of the feedstock compound to form acetic anhydride. The carbonylation process is operated under substantially anhydrous conditions. As used throughout this application "substantially anhydrous," means that acetic anhydride is present in such amounts that any water that may be fed to the carbonylation reactor is present in an amount which is less than the amount necessary to convert all of the acetic anhydride in the reactor to acetic acid.

The feedstock compound is a compound that can react with carbon monoxide to form acetic anhydride through one or more carbonylation reactions. Some examples include esters, ethers and olefins. In some embodiments, the feedstock compound is selected from methyl acetate, dimethyl ether or a combination of the two. In some embodiments, the feedstock compound is methyl acetate.

Carbon monoxide is fed to carbonylation reactors as a gas. In some embodiments, the carbon monoxide is fed in a finely divided form, e.g., by means of a gas sparger, to maximize the concentration of carbon monoxide in the reaction composition. In some embodiments, carbon monoxide is fed to the second carbonylation reactor inside the liquid phase of the liquid feed mixture. The carbon monoxide gas stream may contain other gasses, such as hydrogen. In some embodiments, the carbon monoxide gas contains up to about 7 volume percent hydrogen. The amount of hydrogen in the carbon monoxide varies widely depending on the process and ancillary equipment, and can be selected based on the appropriate balance between the need to have enough hydrogen to preserve catalyst activity without causing excessive tar production that can result from excessive hydrogen in the system. In some embodiments, the carbon monoxide feed contains from about 0.3 to about 15 weight percent hydrogen. In some embodiments, the carbon monoxide feed contains from about 0.5 to about 2.5 weight percent hydrogen. In some embodiments, the carbon monoxide feed contains from about 1.0 to about 2.0 weight percent hydrogen. In some embodiments, the carbon monoxide feed contains from about 5 to about 15 weight percent hydrogen. In some embodiments, the carbon monoxide feed contains from about 5 to about 10 weight percent hydrogen. The weight percent amount of hydrogen present in the feeds may be the same or different. In some embodiments, they differ by 0.5 to 5 weight percentage points.

In a carbonylation reactor, the feedstock compound and carbon monoxide react in the presence of catalyst in the carbonylation reactor to form acetic anhydride. Each carbonylation reactor contains a liquid reaction composition containing (i) any unreacted feedstock compound, (ii) dissolved carbon monoxide and (iii) acetic anhydride product. The liquid reaction composition may contain other components such as iodine-containing compounds, acetic acid, catalyst, ethylidene diacetate, tar, acetone, inert materials, corrosion metals, etc.

The identity of the catalyst used in the process provided by the present invention and the means by which the reactants are placed in presence of the catalyst are not critical and may be selected from any suitable carbonylation catalyst. In some embodiments, the carbonylation catalyst includes at least one Group VIII metal or Group VIII metal compound. The catalyst may also contain combinations of two or more of Group VIII metals or metal compounds. In some embodiments, the catalyst includes two or more Group VII metals or metal compounds. In some embodiments, one or more of the Group VIII metals is a Noble metal. In some embodiments, the metal is selected from nickel, iridium and rhodium or combinations thereof. In some embodiments, the metal component of the carbonylation catalyst is iridium. In some embodiments, the metal component is rhodium. In some embodiments, the metal component is nickel.

In some embodiments, the catalyst is present in a form that is soluble in the reaction compositions. The metal component of such a catalyst system may be provided to the process in various forms such as a metallic state, metal chloride, metal oxide or metal triiodide, metal hydrate, or metal carbonyl complexes, (e.g. $Rh(CO)_2I_2$) from which the soluble, catalytically-active metal complex is formed. See, for example, the catalyst descriptions in U.S. Pat. No. 4,374,070 and Roth et al., *Low pressure process for acetic acid via carbonylation*, Chem. Tech., 1971 p. 600. In some embodiments, the concentration of the dissolved metal in the liquid compositions contained in the carbonylation reactors are about 250 to about 1300 ppm. In some embodiments, the concentration of the metal in the liquid compositions is between about 400 and about 1000 ppm. In some embodiments, the concentration of the metal in the liquid compositions is between about 600 and about 800 ppm. The two carbonylation reactors may have the same or different concentrations. In some embodiments, the catalyst concentration is lower in the second reactor is lower due to additional materials introduced between the reactors and additional gasses in the second reactor. In some embodiments, the metal concentration is about 0.5 to about 50% lower in the second carbonylation reactor. In some embodiments, the metal concentration is about 5 to about 25% lower in the second carbonylation reactor. In some embodiments, the metal concentration is about 10 to about 20% lower in the second carbonylation reactor.

In some embodiments, catalyst is present as part of solid particles in a liquid phase, such as those taught in U.S. Pat. Nos. 6,080,373, 5,880,311 and 5,155,261, which teach a carbonylation system using solid catalyst on which a rhodium complex is supported on a porous, cross-linked vinyl pyridine resin carrier. In some embodiments, solid catalysts which do not rely either upon the presence of iodine-containing compounds or of iodine-containing catalyst components or promoters may be used as carbonylation catalysts.

In some embodiments reaction rates may be increased by the inclusion of a promoter compound in the catalyst. Some examples of promoters include inorganic iodide salts or substances that form one or more iodide salts in the carbonylation reactor. Some examples of substances that form iodide salts include inorganic elements such as alkali or alkali-earth metals, lithium and organophosphorus or organonitrogen compounds. Some examples of organophosphorus or organonitrogen iodides include phosphonium iodides, ammonium iodides and heterocyclic aromatic compounds in which at least one ring hetero atom is a quaternary nitrogen atom. Some examples of such phosphorus- and nitrogen-containing iodides include tetra(hydrocarbyl)phosphonium iodides such as tributyl(methyl)phosphonium iodide, tetrabutylphosphonium iodide, tetraoctyl-phosphonium iodide, triphenyl(methyl)phosphonium iodide, tetraphenylphosphonium iodide and the like; tetra(hydrocarbyl)ammonium iodides such as tetrabutylammonium iodide and tributyl(methyl)ammonium iodide; and heterocyclic aromatic compounds such as N-methylpyridinium iodide, N,N'-dimethylimidazolium iodide, N-methyl-3-picolinium iodide, N-methyl-2,4-litidinium iodide, N-methyl-2,4-lutidinium iodide and N-methylquinolinium iodide. In some embodiments, the iodide salt promoters (that either are added or are formed by reaction of the additive) are selected from lithium iodide and tetraalkylphosphonium iodides, triphenyl(alkyl)phosphonium iodides, tetraalkylammonium iodides and N,N'-dialkylimidazolium iodides wherein the alkyl groups contain up to 8 carbon atoms. Soluble or insoluble oligomers or polymeric resins containing these foregoing functional groups may also be used.

In some embodiments, some or all of the promoter compound is fed as a compound which forms an iodide salt in the carbonylation reactor. Thus, the promoter compounds may be fed initially in the form of their corresponding acetates, hydroxides, chlorides or bromides or the phosphorus- and nitrogen-containing promoters may be fed as compounds in which the phosphorus or nitrogen atoms are trivalent, e.g., tributylphosphine, tributylamine, pyridine, imidazole, N-methylimidazole and the like, which are quaternized by other iodine-containing compounds present in the carbonylation reactor. In some embodiments, lithium promoter is formed by adding lithium hydroxide, lithium acetate, lithium chloride, or lithium bromide.

The amount of the iodide salt promoter present in the carbonylation reactor can be varied substantially depending on a variety of factors, especially the particular promoter used. In some embodiments the concentration of lithium iodide in the reaction composition may range from about 175 to about 5000 ppm Li. In some embodiments the concentration ranges from about 1000 to about 3000 ppm Li. The phosphorus- and nitrogen-containing promoters in some embodiments may be present in much higher concentrations such as about 0.5 to about 25 weight percent, calculated as their iodide salts and based on the total weight of the reaction composition, i.e., the contents of the carbonylation reactor. The two carbonylation reactors may have the same or different concentrations. As with catalyst metals, in some embodiments, the promoter concentration is lower in the second reactor due to additional materials introduced between the reactors and additional gasses in the second reactor. Some examples include about 0.5 to about 50% lower, about 5 to about 25% lower, and about 10 to about 20% lower.

In some embodiments, the catalyst system also includes a transition metal salt as a co-promoter, some examples of which include salts of ruthenium, tungsten, osmium, nickel, cobalt, platinum, palladium, manganese, titanium, vanadium, copper, aluminum, tin, and antimony.

In some embodiments, the components in the reactor are also combined with at least one iodine-containing compound. As used throughout this application, "iodine-containing compounds" means any compounds that include at least one iodine atom. Examples include methyl iodide, elemental iodine, acetyl iodide and hydrogen iodide. "Iodine-containing compounds" may also be a combination of any two or more of the foregoing. In some embodiments, at least one iodine-containing compound is methyl iodide. Some of these iodine-containing compounds may be produced in situ from reactants or recycled process streams. In some embodiments, at least one iodine-containing compound is a compound that will form methyl iodide in situ.

The amounts of various materials, e.g., carbon monoxide methyl feedstock compound, acetic acid, acetic anhydride, iodine containing compounds, etc. present in the reaction composition vary substantially depending, for example, on the carbonylation rate, residence time and concentrations of various components. The two carbonylation reactors may have the same or different concentrations.

In some embodiments, acetic acid is also fed to the carbonylation reactor, where, among other things, it serves as a solvent medium for various components in the various reaction compositions. Other components may also be fed to the carbonylation reactor. For example, in some embodiments acetic anhydride can also be fed to the first carbonylation reactor, e.g., as a solvent or carrier for certain types of catalyst. In some embodiments, methanol or water may also be fed to a carbonylation reactor. In some embodiments, other byproducts of the reaction or from downstream or other processes can also be fed to the carbonylation reactor as part of a recycle or recovery stream. Similarly, in some embodiments, all or part of any of the other components fed to the reactors (e.g. acetic acid, catalyst, feedstock compound, or combinations of two or more of these) can be fed in whole or in part as part of a recycled or recovered stream and from byproducts of the reaction or from downstream or other processes.

In some embodiments, the first and second carbonylation reactors are separate vessels. Such vessels can be selected from any suitable pressure vessel or part thereof and may be provided, for example, with means for agitation. The vessel design may be a pipe reactor, column, tank, bubble column, stirred tank or other suitable design. In some embodiments, the first and second carbonylation reactors are generally columnar vessels equipped with one or more internal baffles which, in combination with the carbon monoxide gas sparger feed device, create a highly agitated, recirculating reaction composition. In some embodiments, the residence time of the feedstock compound within each carbonylation reactor is at least about 4 minutes. In some embodiments, residence time is in the range of about 4 minutes to about 50 minutes. In some embodiments, residence time is in the range of about 10 minutes to about 120 minutes. In some embodiments, residence time is in the range of about 15 to about 50 minutes. In some embodiments, residence time is in the range of about 20 to about 40 minutes. In some embodiments, residence time is in the range of about 20 to about 30 minutes. In some embodiments, residence time is in the range of about 30 to about 45 minutes. The design and residence time in the two carbonylation reactors may be the same or different. In some embodiments, the residence time in the second reactor (adjusted for any geometric differences between two reactors) is about 0.5 to about 50% less than in the first reactor. In some embodiments, the range may be about 5 to about 25% lower or about 10 to about 20% lower.

In some embodiments, one or both of the carbonylation reactors are maintained at elevated temperature such as about 100 to about 300° C.; in some embodiments, about 150 to about 250° C.; in some embodiments, about 175 to about 220° C. In some embodiments, one or both carbonylation reactors run a pressure (total) of about 21 to about 277 bars absolute (bara; about 300 to about 4000 pounds per square inch gauge (psig)); in some embodiments, about 35.5 to about 104.4 bara (about 500 to about 1500 psig). The temperature and pressure of the two carbonylation reactors may be the same or different, depending on factors such as process control considerations and process configurations. In some embodiments, the second reactor has a higher pressure; in others, a lower pressure; still others, the same pressure. The same is true for temperature. In some embodiments, the second reactor is operated at a temperature that is 1-10° C. lower; in others, 1-10° C. higher. Similarly, in some embodiments, the second reactor is operated at a pressure that is 50 to 100 psi higher; in other embodiments, the second reactor is operated at a pressure that is 50 to 100 psi lower.

First Carbonylation Step

The first carbonylation step of the process is carried out by continuously feeding the components mentioned above to the first carbonylation reactor. Catalyst may be part of the feed or already present in the reactor (the latter being the case in some heterogeneous catalyst embodiments). This results in the formation of a first liquid reaction composition containing at least the following: (i) feedstock compound, (ii) dissolved carbon monoxide and (iii) acetic anhydride product. In some embodiments it may also contain an iodine-containing compound (such as methyl iodide) catalyst, acetic acid, or a combination of two or more of the foregoing. This first reaction composition can be removed from the first carbonylation reactor and fed to the esterification zone. In some embodiments, the first reaction composition contains about 8 to about 38 weight percent acetic anhydride. In some embodiments, the first reaction composition contains about 10 to about 30 weight percent acetic anhydride. In some embodiments, the first reaction composition contains about 15 to about 60 weight percent feedstock compound. In some embodiments, the first reaction composition contains about 19 to about 50 weight percent feedstock compound. In some embodiments, the first reaction composition contains about 6 to about 25 weight percent methyl iodide. In some embodiments, the first reaction composition contains about 8 to about 22 weight percent methyl iodide. In some embodiments, the first reaction composition contains about 18 to about 40 weight percent acetic acid. In some embodiments, the first reaction composition contains about 24 to about 34 weight percent acetic acid. Any combination of the foregoing is within the scope of the invention. Thus, for example, embodiments exist in which the first reaction composition contains about 8 to about 38 weight percent acetic anhydride, about 15 to about 60 weight percent feedstock compound, about 6 to about 25 weight percent methyl iodide, and about 18 to about 40 weight percent. As another example, embodiments exist in which the first reaction composition contains about 10 to about 30 weight percent acetic anhydride, about 19 to about 50 weight percent feedstock compound, about 8 to about 22 weight percent methyl iodide, about 24 to about 34 weight percent acetic acid.

Esterification

At least part of the first liquid reaction composition is continuously removed from the first carbonylation reactor and fed to an esterification zone. In at least a portion of the esterification zone, methanol is combined with at least part of the first liquid reaction composition under conditions effective to cause at least some of the acetic anhydride to react with methanol, resulting in the second liquid reaction composition. The methanol and acetic anhydride react to form methyl acetate and acetic acid. Methanol can be introduced at any location in the esterification zone. At least some of the methanol reacts with the acetic anhydride component of the first reaction composition. The methanol reacts exothermically with acetic anhydride present in the reaction composition.

As used throughout this application, "esterification zone" refers to the piping through which the first liquid reaction composition leaves the first carbonylation reactor and all subsequent equipment and piping through which the liquid stream flows (even during and after it is combined with methanol and converted to a second liquid reaction composition) prior to introduction into the second carbonylation reactor. In some embodiments, the esterification zone includes one or more heat exchangers and associated conduits wherein heat generated by both the carbonylation and esterification reactions is removed from the product stream.

Methanol may be fed directly to one or more heat exchangers, to a conduit or pipe upstream or downstream of one or more heat exchangers, or both. In some embodiments, the esterification zone includes at least one heat exchanger upstream of the point at which methanol is combined with the first liquid reaction composition and at least one heat exchanger downstream of the point at which methanol is combined with the first liquid reaction composition.

The amount of methanol added depends on a variety of factors such as the dimensions of the equipment involved and the amount of acetic acid that is desired. In some embodiments, the amount of methanol is greater than 0 and less than 1 mole of methanol per mole acetic anhydride present in the reaction composition removed from the first carbonylation reactor. In some embodiments, the amount of methanol fed to the esterification zone may be greater than 1 mole methanol per mole acetic anhydride present in the reaction composition removed from the first carbonylation reactor, thereby yielding a second liquid reaction composition with methanol present. In some embodiments, the amount of methanol fed in to the esterification zone is about 0.6 to about 0.85 moles methanol per mole acetic anhydride present in the reaction composition removed from the first carbonylation reactor. In some embodiments, the amount of methanol fed to the esterification zone is sufficient to create a stoichiometric excess of moles of methanol, i.e. more moles per unit time than the number of moles per unit time of acetic anhydride fed to the esterification zone.

Coolant is fed to the heat exchanger(s) of the esterification zone to reduce the temperature of the product solution of the esterification zone. In some embodiments, the coolant is water having a temperature of about 20 to about 110° C. However, any effective or desired coolant and any desired temperature can be used. In some embodiments, cooling water is fed to the heat exchanger and converted to steam to recover the heat generated by the exothermic carbonylation and esterification reactions. In some embodiments, this steam has a pressure between about 0.1 and about 14.5 bars gauge (barg). In some embodiments, the steam has a pressure between about 0.9 and about 1.4 bars gauge (barg). In some embodiments, recovered steam is used elsewhere in the acetic acid/acetic anhydride process. Some examples are distillation towers or flash evaporators. In some embodiments, the steam is used as 1 barg steam supplied to the reboiler of one or more distillation columns. This provides increased heat integration in the process.

Second Carbonylation Step

The product solution from the esterification zone is fed continuously to a second carbonylation reactor, the operation of which is described hereinabove along with carbon monoxide and in the presence of catalyst (and optionally other compounds such as methyl iodide) to cause the conversion of feedstock compound to additional acetic anhydride. In some embodiments, the carbon monoxide is fed in a finely divided form, e.g., by means of a gas sparger, to maximize the concentration of carbon monoxide in the reaction composition. In some embodiments, carbon monoxide is fed to the second carbonylation reactor inside the liquid phase of the liquid feed mixture.

An effluent is continuously removed from the second carbonylation reactor. The composition of the effluent, i.e., the second reaction composition removed from the second carbonylation reactor, in some embodiments contains about 10 to about 50 weight percent acetic anhydride and in some embodiments about 17 to 40 weight percent acetic anhydride. In some embodiments the composition contains about 10 to about 50 weight percent feedstock compound, and in some embodiments about 16 to 40 weight percent feedstock compound. In some embodiments the composition contains about 5 to about 25 weight percent methyl iodide, and in some embodiments about 8 to 20 weight percent methyl iodide. In some embodiments the composition contains about 10 to about 50 weight percent acetic acid, and in some embodiments the composition contains about 20 to about 41 weight percent acetic acid.

Further Processing

The effluent from the second carbonylation reactor may be further processed as desired, and the type of further processing is not critical to the invention. Some possible examples of further processing include separation and purification of components, further carbonylation and/or esterification reactions, recovery and recycle of components, and removal of undesired byproducts. In some embodiments, the effluent is conveyed directly to a flash evaporator zone wherein it is separated into a major vapor fraction containing methyl iodide (if present), methyl acetate and/or dimethyl ether, acetic acid and acetic anhydride and a minor fraction containing a solution of catalyst components in a mixture of acetic acid and acetic anhydride. In some embodiments, separation includes distillation processes, decanting processes, or molecular sieves. The minor fraction is recycled to the carbonylation reactor and the major fraction is separated by a series of distillations into its component parts. As a further example, the effluent from the second carbonylation reactor first may be fed to subsequent carbonylation reactors wherein dissolved carbon monoxide reacts with feedstock compound, e.g., as described in U.S. Pat. No. 5,922,911, to increase the utilization of carbon monoxide in the overall process.

EXAMPLE

The process of the present invention is further illustrated by the following example wherein the parts and percentages of materials are given in parts by weight unless otherwise stated. Materials are fed continuously at the rates shown to a first carbonylation reactor, which is a baffled, back-mixed reaction vessel to which a carbon monoxide stream is fed below the surface of the reaction composition by means of a gas sparger device. Carbon monoxide is fed at the rate of about 7.14 parts per minute; methyl acetate at about 41.0 parts per minute; methyl iodide at about 12.2 parts per minute; acetic acid at about 28.7 parts per minute; and acetic anhydride at about 1.5 parts per minute. Rhodium and lithium catalyst components are present in solution in the acetic acid/acetic anhydride feed and give a concentration of 400 to 1000 ppm [Rh] and 1000 to 2500 ppm [Li] in the liquid mixture contained in the first carbonylation reactor. The capacity of the first carbonylation reactor is designed to give a residence time of approximately 30 minutes. A temperature of about 190 to 210° C. and a total pressure of about 40 to 55 bara are maintained in the first carbonylation reactor.

A first liquid reaction composition is withdrawn continuously from the first carbonylation reactor at a rate of approximately 100.0 parts per minute and fed via conduits to the first of a series of two heat exchangers. The composition of the first liquid reaction composition is approximately 24% methyl acetate, 12% methyl iodide, 29% acetic acid, 25% acetic anhydride and 0.6% dissolved carbon monoxide. The remainder of the first liquid reaction composition contains other components such as ethylidene diacetate, tar, acetone, inert materials, etc. Utility water is fed in the first of a series of two steam generating heat exchangers and is converted to steam. The first heat exchanger is sized to cool the first liquid reaction composition to a temperature of about 133° C. while generating steam at a temperature of approximately 123° C. Methanol is combined with the first liquid reaction composition at a rate of about 5.7 parts per minute in a conduit at a location after the first liquid reaction composition exits the first heat exchanger but before it enters the second heat exchanger. The methanol mixes and reacts with acetic anhydride in the first liquid reaction composition, consuming methanol and acetic anhydride and generating methyl acetate and acetic acid. Due to the exothermic nature of the reaction, the temperature of this second (esterification) liquid reaction composition rises to about 181° C. before entering the second heat exchanger. Utility water is fed to the second of the two steam-generating heat exchangers and is converted to steam. The second heat exchanger is sized to cool the second (esterification) liquid reaction composition to a temperature of about 143° C. while generating steam at a temperature of approximately 133° C.

The second (esterification) liquid reaction composition is removed from the second of the two heat exchangers and fed to a second carbonylation reactor at a rate of about 105.7 parts per minute. The composition of the second (esterification) liquid reaction composition is approximately 35% methyl acetate, 12% methyl iodide, 37% acetic acid and 6% acetic anhydride. The remainder of the second liquid reaction composition contains other components such as ethylidene diacetate, tar, acetone, inert materials, etc. The dimensions, design, and operating conditions of the second carbonylation reactor are essentially identical to those described above for the first carbonylation reactor, though slight variations in pressure, temperature, and composition of the gas stream may occur during normal operations.

A third liquid reaction composition is withdrawn continuously from the second carbonylation reactor at a rate of approximately 111.0 parts per minute. The composition of the third liquid reaction composition is approximately 21% methyl acetate, 11% methyl iodide, 36% acetic acid, 23% acetic anhydride and 0.5% dissolved carbon monoxide. The remainder of the third liquid reaction composition consists of other components such as ethylidene diacetate, tar, acetone, inert materials, etc.

The invention has been described in detail with particular reference to preferred embodiments thereof, but it will be understood that variations and modifications can be effected within the spirit and scope of the invention.

We claim:

1. A process for the coproduction of acetic anhydride and acetic acid in the liquid phase under substantially anhydrous conditions which comprises the steps of:
   (1) continuously combining in a first carbonylation reactor components comprising: (i) at least one feedstock compound selected from methyl acetate, dimethyl ether or a combination thereof; and (ii) a first carbon monoxide stream, to produce a first liquid reaction composition, wherein:
      the components are combined in the presence of a carbonylation catalyst,
      the components are combined under conditions effective to convert at least some of the feedstock compound to acetic anhydride, and
      the first liquid reaction composition comprises: (i) at least some unreacted feedstock compound, (ii) dissolved carbon monoxide and (iii) acetic anhydride product;
   (2) continuously removing at least part of the first liquid reaction composition from the first carbonylation reactor and contacting the at least part of the first liquid reaction composition with methanol in an esterification zone to form a second liquid reaction composition in a liquid phase under conditions effective to cause at least some of the acetic anhydride from the first reaction composition and at least some of the methanol to react to produce methyl acetate and acetic acid in the second liquid reaction composition, wherein the esterification zone comprises at least one heat exchanger configured to remove some heat from the first liquid reaction composition, the second liquid reaction composition, or both;
   (3) continuously feeding the second liquid reaction composition to a second carbonylation reactor along with carbon monoxide to produce a third liquid reaction composition in a liquid phase, wherein:
      the second liquid reaction composition and a second carbon monoxide stream are combined under conditions effective to cause at least some unreacted feedstock compound, methyl acetate from (2), or both to be converted to acetic anhydride, and
      the third reaction composition comprises (i) unreacted feedstock compound, methyl acetate from (2) or both, (ii) acetic acid, and (iii) acetic anhydride product, and
   (4) continuously removing the third liquid reaction composition from the second carbonylation reactor.

2. The process of claim 1, where the at least one heat exchanger converts water into steam.

3. The process of claim 1, wherein at least one of the carbonylation reactors is operated at a temperature of about 100 to about 300° C. and a pressure (total) of about 21.7 to about 276.7 bars absolute (bara) and the residence time within the carbonylation reactors is about 4 minutes to about 120 minutes.

4. The process of claim 1, wherein the carbonylation reactors are operated at a temperature of about 175 to 220° C. and a pressure (total) of about 35.5 to about 104.4 bara, the residence time within the carbonylation reactors is about 15 to about 40 minutes, the composition of the first reaction composition removed from the first carbonylation reactor and fed to the esterification zone of step (2) is about 8 to about 38 weight percent acetic anhydride, about 15 to about 60 weight percent feedstock compound, about 6 to 25 weight percent methyl iodide, about 18 to about 40 weight percent acetic acid.

5. The process of claim 1, wherein the amount of methanol fed to the esterification zone is about 0.6 to about 0.85 moles per mole of acetic anhydride fed via the first reaction composition to the esterification zone.

6. The process of claim 1, wherein the amount of methanol fed to the esterification zone is above zero but less than about 1 moles per mole of acetic anhydride fed via the first reaction composition to the esterification zone.

7. The process of claim 1, wherein the amount of methanol fed to the esterification zone is sufficient to create a stoichiometric excess of moles of methanol against the moles of acetic anhydride fed to the esterification zone.

8. The process of claim 1, wherein the process further comprises feeding acetic acid to the first carbonylation reactor.

9. The process of claim 1, wherein the carbonylation catalyst comprises rhodium or a rhodium compound.

10. The process of claim 1, wherein the components combined in the first carbonylation reactor further comprise at least one iodine-containing compound.

11. The process of claim 10, wherein the at least one iodine-containing compound is methyl iodide or a compound that forms methyl iodine in the first liquid reaction composition.

12. The process of claim 1, wherein at least some of the carbonylation catalyst dissolves in the first liquid reaction composition.

13. The process of claim 1, wherein at least some of the carbonylation catalyst is a solid in the presence of the first liquid reaction composition.

14. The process of claim 1, wherein the first carbon monoxide stream is fed at a location inside the first liquid reaction composition.

15. The process of claim 1, wherein the second carbon monoxide stream is fed at a location inside the third liquid reaction composition.

16. A process for the coproduction of acetic anhydride and acetic acid in the liquid phase under substantially anhydrous conditions which comprises the steps of:
(1) continuously combining in a first carbonylation reactor components comprising: (i) at least one feedstock compound selected from methyl acetate, dimethyl ether or a combination thereof; (ii) a first carbon monoxide stream; (iii) acetic acid; and (iv) an iodine-containing compound, to produce a first liquid reaction composition, wherein:
the components are combined in the presence of a carbonylation catalyst that is dissolved in the first liquid reaction composition,
the components are combined under conditions effective to convert at least some of the feedstock compound to acetic anhydride, and
the first liquid reaction composition comprises: (i) at least some unreacted feedstock compound, (ii) dissolved carbon monoxide and (iii) acetic anhydride product;
(2) continuously removing at least part of the first liquid reaction composition from the first carbonylation reactor and contacting the at least part of the first liquid reaction composition with methanol in an esterification zone to form a second liquid reaction composition in a liquid phase under conditions effective to cause at least some of the acetic anhydride from the first reaction composition and at least some of the methanol to react to produce methyl acetate and acetic acid in the second liquid reaction composition wherein the esterification zone comprises at least one heat exchanged configured to remove some heat from the first liquid reaction composition, the second liquid reaction composition, or both;
(3) continuously feeding the second liquid reaction composition to a second carbonylation reactor along with carbon monoxide to produce a third liquid reaction composition in a liquid phase, wherein:
the second liquid reaction composition and a second carbon monoxide stream are combined under conditions effective to cause at least some unreacted feedstock compound, methyl acetate from (2), or both to be converted to acetic anhydride, and
the third reaction composition comprises (i) unreacted feedstock compound, methyl acetate from (2) or both, (ii) acetic acid, and (iii) acetic anhydride product, and
(4) continuously removing the third liquid reaction composition from the second carbonylation reactor.

17. The process of claim 16, where the at least one heat exchanger converts water into steam.

18. The process of claim 16, wherein at least one of the carbonylation reactors is operated at a temperature of about 100 to about 300° C. and a pressure (total) of about 21.7 to about 276.7 bars absolute (bara) and the residence time within the carbonylation reactors is about 4 minutes to about 120 minutes.

19. The process of claim 16, wherein the carbonylation reactors are operated at a temperature of about 175 to 220° C. and a pressure (total) of about 35.5 to about 104.4 bara, the residence time within the carbonylation reactors is about 15 to about 40 minutes, the composition of the first reaction composition removed from the first carbonylation reactor and fed to the esterification zone of step (2) is about 8 to about 38 weight percent acetic anhydride, about 15 to about 60 weight percent feedstock compound, about 6 to 25 weight percent methyl iodide, about 18 to about 40 weight percent acetic acid.

20. The process of claim 16, wherein the amount of methanol fed to the esterification zone is about 0.6 to about 0.85 moles per mole of acetic anhydride fed via the first reaction composition to the esterification zone.

21. The process of claim 16, wherein the amount of methanol fed to the esterification zone is above zero but less than about 1 moles per mole of acetic anhydride fed via the first reaction composition to the esterification zone.

22. The process of claim 16, wherein the amount of methanol fed to the esterification zone is sufficient to create a stoichiometric excess of moles of methanol against the moles of acetic anhydride fed to the esterification zone.

23. The process of claim 16, wherein the carbonylation catalyst comprises rhodium or a rhodium compound.

24. The process of claim 16, wherein the at least one iodine-containing compound is methyl iodide or a compound that forms methyl iodine in the first liquid reaction composition.

25. The process of claim 16, wherein the first carbon monoxide stream is fed at a location inside the first liquid reaction composition.

26. The process of claim 16, wherein the second carbon monoxide stream is fed at a location inside the third liquid reaction composition.

27. The process of claim 1, wherein the carbon monoxide fed to the second carbonylation reactor is inside the liquid phase of the second liquid reaction composition.

28. The process of claim 16, wherein the carbon monoxide fed to the second carbonylation reactor is inside the liquid phase of the second liquid reaction composition.

* * * * *